US006939302B2

(12) United States Patent
Griffiths et al.

(10) Patent No.: US 6,939,302 B2
(45) Date of Patent: Sep. 6, 2005

(54) APPARATUS AND METHOD FOR CONTROLLING CONTRAST ENHANCED IMAGING PROCEDURES

(75) Inventors: David M. Griffiths, Pittsburgh, PA (US); Arthur E. Uber, III, Pittsburgh, PA (US)

(73) Assignee: MEDRAD, Inc., Indianola, PA (US)

( * ) Notice: Subject to any disclaimer, the term of this patent is extended or adjusted under 35 U.S.C. 154(b) by 369 days.

(21) Appl. No.: 10/034,266

(22) Filed: Oct. 19, 2001

(65) Prior Publication Data

US 2002/0055682 A1 May 9, 2002

Related U.S. Application Data

(62) Division of application No. 09/267,238, filed on Mar. 12, 1999, now Pat. No. 6,317,623.

(51) Int. Cl.[7] .................................................. A61B 8/14
(52) U.S. Cl. ........................................................ 600/458
(58) Field of Search ................................ 600/407–472, 600/504; 424/9.51–9.53, 422, 9.32, 491, 9.4; 514/169

(56) References Cited

U.S. PATENT DOCUMENTS

| 4,477,923 A | | 10/1984 | Baumann et al. | |
|---|---|---|---|---|
| 5,194,300 A | * | 3/1993 | Cheung | 427/213.31 |
| 5,230,343 A | * | 7/1993 | Guberek et al. | 600/504 |

(Continued)

FOREIGN PATENT DOCUMENTS

| DE | 32 03 594 A1 | 8/1983 |
|---|---|---|
| DE | 197 02 896 A1 | 7/1997 |
| DE | 196 47 701 A1 | 5/1998 |
| EP | 0 650 738 A1 | 5/1995 |
| EP | 0 702 966 A2 | 3/1996 |
| GB | 2328745 | 3/1999 |

OTHER PUBLICATIONS

"A Particulate Contrast Agent With Potential For Ultrasound Imaging Of Liver", Ultrasound in Med. & Biol., vol. 13 No. 9, pps. 555–556, 1987.
"Selective Destruction of Contrast Agent Microspheres", Ayache Bouakaz, et al.; IEEE Ultrasonics Symposium (1995).
"Effect of Ultrasound on the Release of Micro–Encapsulated Drugs", Peter J.A. Frinking, et al.; Ultrasonics 36; pp., 709–712; (1998).
"A Particulate Contrast Agent With Potential For Ultrasound Imaging Of Liver", Ultrasound in Med. & Biol., vol. 13 No. 9, pp. 555–556, 1987.

*Primary Examiner*—Ali Imam
(74) *Attorney, Agent, or Firm*—Gregory L. Bradley; James R. Stevenson; Henry E. Bartony, Jr.

(57) ABSTRACT

A system for delivery of a medium having ultrasound contrast enhancement agents therein to a patient includes a pressurizing device for pressurizing the medium, a fluid path connecting the pressurizing device to the patient and a concentration sensor in communication with the fluid path. The concentration of the contrast enhancement agents is measured by the concentration sensor during injection of the medium into the patient to assist in controlling the delivery system and/or an imaging procedure.

21 Claims, 3 Drawing Sheets

U.S. PATENT DOCUMENTS

| | | | |
|---|---|---|---|
| 5,281,408 A | * | 1/1994 | Unger ........................ 424/9.4 |
| 5,310,540 A | * | 5/1994 | Giddey et al. ............. 424/9.52 |
| 5,383,858 A | | 1/1995 | Reilly et al. |
| 5,413,774 A | * | 5/1995 | Schneider et al. ......... 424/9.51 |
| 5,445,832 A | * | 8/1995 | Orsolini et al. ............. 424/491 |
| 5,469,849 A | | 11/1995 | Sasaki et al. |
| 5,544,215 A | | 8/1996 | Shroy, Jr. et al. |
| 5,569,181 A | | 10/1996 | Heilman et al. |
| 5,601,086 A | | 2/1997 | Pretlow, III et al. |
| 5,611,344 A | | 3/1997 | Bernstein et al. |
| 5,806,519 A | | 9/1998 | Evans, III et al. |
| 5,827,504 A | | 10/1998 | Yan et al. |
| 5,840,026 A | | 11/1998 | Uber, III et al. |
| 5,846,517 A | | 12/1998 | Unger |
| 5,868,710 A | | 2/1999 | Battiato et al. |
| 5,885,216 A | * | 3/1999 | Evans et al. ................. 600/431 |
| 6,514,203 B2 | * | 2/2003 | Bukshpan .................... 600/439 |
| 6,527,718 B1 | * | 3/2003 | Connor et al. .............. 600/439 |

\* cited by examiner

APPARATUS AND METHOD FOR CONTROLLING CONTRAST ENHANCED IMAGING PROCEDURES

CROSS REFERENCE TO RELATED APPLICATION

This application is a division of application Ser. No. 09/267,238, filed on Mar. 12, 1999, now U.S. Pat. No. 6,317,623 the contents of which are hereby incorporated by reference.

BACKGROUND OF THE INVENTION

The present invention relates generally to the control of contrast enhanced imaging procedures, and, more particularly, to apparatuses, systems and methods for controlling an imaging procedure in which contrast agents are delivered to a patient.

Ultrasound imaging creates images of the inside of the human body by broadcasting ultrasonic energy into the body and analyzing the reflected ultrasound energy. Differences in reflected energy are made to appear as differences in gray scale or color on the output images. As with other medical imaging procedures, contrast enhancing fluids (often referred to as contrast media) can be injected into the body to increase the difference in the reflected energy and thereby increase the contrast displayed in the image (that is, the image contrast) viewed by the operator.

For ultrasound imaging, the most common contrast media contain many small bubbles (sometimes referred to as microbubbles) suspended therein. The difference in density of bubbles when compared to water, and thus their difference in sound transmissivity, makes small gas bubbles excellent means for scattering ultrasound energy. Small solid particles can also serve to scatter ultrasonic energy. Such particles are typically on the order of 1 to 10 microns (that is, $10^{-6}$ to $10^{-5}$ meters) in diameter. These small particles can pass safely through the vascular bed and, in some cases, traverse the pulmonary circulation. Contrast agents are also used for non-vascular applications such as assessment of tubal patency in gynecological applications.

Contrast media suitable for use in ultrasound are supplied in a number of forms. Some of these contrast media are powders to which liquid is added just before use. The powder particles cause gas bubbles to coalesce around them. The powder must be mixed with a liquid, and the mixture must be agitated with just the right amount of vigor to obtain the optimum creation of bubbles. Another type of contrast medium is supplied in a liquid form that requires hypobaric or pressure activation. A third type of contrast medium is a liquid that is agitated vigorously. There are no solid particles to act as nuclei, but the liquid is a mixture of several liquid components that make relatively stable small bubbles. A fourth type of contrast medium uses "hard" spheres filled with a gas. These contrast media are typically supplied as a powder that is mixed with a liquid. The goal is to suspend the spheres in the liquid without breaking them. Even though such spheres have a shell that is hard compared to a liquid, they are very small and relatively fragile. It is also possible for the solid particles themselves to act to scatter ultrasonic energy, but the acoustical properties of the solid spheres are not as different from water as those of a gas. However, solid particles have the advantage that they are much more robust and long lasting.

Suspended or dispersed entities such as microbubbles (liquid or gas), microspheres and solid particles suitable to enhance ultrasonic imaging contrast are referred to herein as contrast enhancement agents/particles. With these agents there are several problems, including: (1) Variations in the preparation process (mixing, agitation, pressure activation) can lead to variations in microsphere or particle concentration that affect the resulting imaging procedure; (2) Some agents deteriorate with time after preparation, causing the concentration of the microbubbles or particles to decrease; and (3) Microbubble agents can also be adversely affected by pressure before or during administration, causing microbubble destruction by increasing gas diffusion rates or damage to the encapsulation shell from delivery or pressure effects. This may also affect the microbubble concentration.

Contrast enhancement agents also enhance other modes of ultrasonic imaging. For example, when the microbubbles, microspheres or particles are carried along in the blood stream, the reflected energy is Doppler shifted. This Doppler shift allows an estimation of the speed of blood flow. Bubbles can also be excited so that they radiate ultrasonic energy at a harmonic of the incident ultrasonic energy. This harmonic imaging with the use of contrast medium can be used to increase the effectiveness of the contrast agent.

After mixing/preparation as described above, the contrast medium is drawn into a syringe or other container for injection into the patient. Typically, the fluid is injected into the vein in the arm of the patient. The blood dilutes and carries the contrast medium throughout the body, including to the area of the body being imaged (that is, the region-of-interest or ROI). As mentioned above, the contrast medium can also be injected into other body cavities or tissues as necessary for diagnostic or therapeutic activities.

It is becoming more common for a microprocessor-controlled, powered injector to be used for injecting the contrast medium. The use of such powered injectors has the benefit of maintaining a consistent flow over a long time, thereby providing a consistent amount of contrast medium in the blood stream. If there are too few contrast enhancement particles per unit volume in the flow, however, there will be insufficient image enhancement and the diagnosis cannot be made. If too many contrast enhancement particles are present, too much energy is reflected, resulting in blooming or saturation of the ultrasound receiver.

Thus, although a power injector can inject contrast medium at a constant flow rate, there must generally be a constant number of contrast enhancement agents per volume of fluid injected to provide a constant image contrast. Because a gas is significantly less dense than water and other liquids, however, gas bubbles will rise in a liquid. The rate of rise is related to the diameter of the gas bubble. This density difference provides a useful tool to quickly separate large bubbles created during the initial mixing. However, the small bubbles desired for image enhancement will also rise slowly. Solid particles, on the other hand, will tend to settle or sink because most solids are denser than water. Many minutes can elapse between the initial mixing of the contrast medium and the injection into the patient, or the injection itself may be several minutes in duration. If the concentration of particles changes, the image contrast will be degraded as mentioned above.

There are also many other reasons why the number of contrast enhancement agents per volume of a certain contrast medium (and thereby the image contrast) can vary during an injection procedure. For example, the initial mixing may not have resulted in a homogeneous dispersion or suspension. Likewise, bubbles or microspheres of certain contrast media can be destroyed under conditions experienced in mixing/preparation, storage or delivery of the contrast media.

It is, therefore, very desirable to develop systems and methods to control the concentration of contrast enhancing agents delivered to a patient in an ultrasound imaging procedure.

SUMMARY OF THE INVENTION

The present invention provides systems, apparatuses and methods for delivery of a medium having, for example, ultrasound contrast enhancement agents therein to a patient. The present invention includes a pressurizing unit, such as a pump, for pressurizing the medium, a fluid path connecting the pump to the patient and a sensor in communication with the fluid path.

In an embodiment, the present invention includes a system for delivery of a medium with contrast enhancement agents therein into a patient. The system includes a container to hold the medium, a pressurizing device for pressurizing the medium in the container, a fluid path connecting the pressurizing device to the patient, and a sensor in communication with at least one of the container, the pressurizing device or the fluid path. The sensor is operable to measure a property of the contrast enhancement agents.

The properties that may be measured by the sensor include, but are not limited to, concentration and size distribution. Further, for example, the concentration of the contrast enhancement agents may be measured by the sensor before or during injection of the medium into the patient.

In a preferred embodiment, the sensor measures the properties of the contrast enhancement agents to control the preparation of the medium, the delivery of the medium and/or an imaging procedure carried out in conjunction with delivery of the medium.

The contrast media contains contrast enhancement agents which interact with the energy beamed into the body for creation of the image. The energy can be ultrasonic or electromagnetic. Common electromagnetic energies include X-rays and light. The contrast enhancement agents include but are not limited to microbubbles—with or without a solid core or nucleus, microspheres with relatively rigid shells filled with gas or liquid, liposomes with relatively flexible shells filled with gas or liquid, solid micro-particles, or microspheres of a liquid that are not miscible with the liquid in the contrast media. Any contrast media involving two immiscible materials or different phases of material could benefit from this invention. Contrast media where the molecules of the contrast enhancing material dissolve in the liquid of the contrast media can benefit from this invention to the extent that they are mixed from two different phases or to the extent that they might separate during storage or use.

The present invention preferably further includes a communication unit for transmitting data corresponding to the measured concentration or other property of the contrast enhancement agents. A user interface (including, for example, a display unit) in communicative connection with the communication unit may be used to provide the concentration or other data to an operator. The user interface can also be adapted for input of data by the operator.

Preferably, the present invention also includes a processing unit in communicative connection with the communication unit. This processing unit preferably includes a control unit adapted to transmit a control signal based at least in part on the concentration or other data received from the communication unit.

The present invention may also include a pump controller to control the pressurizing of the injection medium. The pump controller is preferably in communicative connection with the processing unit so that the operation of the pump controller is responsive to (that is, controlled by) the control signal from the processing unit.

The present invention preferably further includes an imaging unit such as an ultrasound scanning unit to produce a contrast enhanced image of the patient. The imaging unit is preferably in communicative connection with the processing unit so that the operation of the imaging unit is responsive to or controlled by the control signal from the processing unit. The imaging unit can also be adapted to transmit a signal corresponding to properties of the image to the processing unit so that other delivery operations can be controlled based upon the signal from the imaging unit.

The present invention may further include an agitation mechanism to agitate the medium before or during injection of the medium. The agitation mechanism is preferably in communicative connection with the processing unit so that the operation of the agitation mechanism is responsive to or controlled by the control signal received from the processing unit.

In the case, for example, that the contrast enhancement agents comprise microbubbles or microspheres suspended in the medium, the present invention may further include a contrast enhancement agent concentration regulator that is operable to dilute, damage or destroy a controlled portion of microbubbles or microspheres to control the concentration thereof. The bubble concentration regulator is preferably in communicative connection with the processing unit so that the operation of the bubble concentration regulator can be responsive to or controlled by the control signal from the processing unit.

The present invention also provides a method of delivering a medium with contrast enhancement agents therein into a patient. The method comprises the step of measuring a property (for example, the concentration or size distribution) of the contrast enhancement agents before or during delivery of the medium to the patient to control the delivery.

Further, the present invention provides a method of preparing a medium with contrast enhancement agents therein. The method comprises the step of measuring the concentration or other property of the contrast enhancement agents during preparation of the medium to assist in properly preparing the medium. Likewise, the present invention provides a system for preparing a contrast medium with contrast enhancement agents therein comprising a mixing container, an agitation mechanism for agitating the contents of the mixing container and a sensor adapted to measure the concentration or other property of the contrast enhancement agents in the container.

The present invention still further provides a fluid path element to cooperate with a system for delivery of a medium with contrast enhancement agents therein into a patient. The system includes a pressurizing device for pressurizing the medium, a fluid path connecting the pressurizing device to the patient, and a sensor, such as a concentration sensor, in communication with the at least one of the pressurizing device or the fluid path. The concentration or other property of the contrast enhancement agents is measured by the sensor (before or during delivery of the medium into the patient). The fluid path element preferably includes a conduit through which the fluid can flow, and a coupler to physically mate with the concentration sensor. The coupler is preferably fabricated from an injection-molded polymeric material.

Known and repeatable concentration of contrast enhancement agents such as microbubble agents is important from preparation to preparation of contrast media to gain consistent imaging results. The present invention can operate in conjunction with an injection system (automated or manual) to measure the concentration and/or size distribution of such contrast enhancement agents before or during injection. The resultant information/signal on agent concentration and/or size distribution can be used, for example, to correct images for diagnostic utility or be used in real-time with an automated injection system to dynamically control flow rate and more precisely control agent delivery and the vascular concentration of the agent. Concentration and/or size distribution information can also be used to control microbubble concentration and/or size in the delivery path either by mixing or controlled bubble regulation/destruction before the agent is injected into the patient. By delivering known concentrations and size distributions of agents, the time course of enhancement can be observed, opening the way to measuring dose response and to indicator dilution applications of ultrasound contrast. At the very least, the measurement can be used to indicate when an enhancement agent has been damaged or may be ineffective, preventing a useless or sub-optimal imaging procedure.

The present invention and its attendant advantages will be further understood by reference to the following detailed description and the accompanying drawings.

DETAILED DESCRIPTION OF THE INVENTION

Many enhancement agents typically have a microbubble concentration on the order of approximately $1\times10^8$ to $1\times10^9$ particles per ml. Mean bubble size for currently available transpulmonary agents typically range from approximately 2 to 10 $\mu$m. Microbubble concentration and size distribution influence the image enhancement achieved. The present inventors have discovered that certain techniques such as optical and ultrasound techniques can be used to measure contrast enhancement agent concentration and/or size distribution to better control numerous aspects of the operation of a contrast delivery system.

Figure 1:
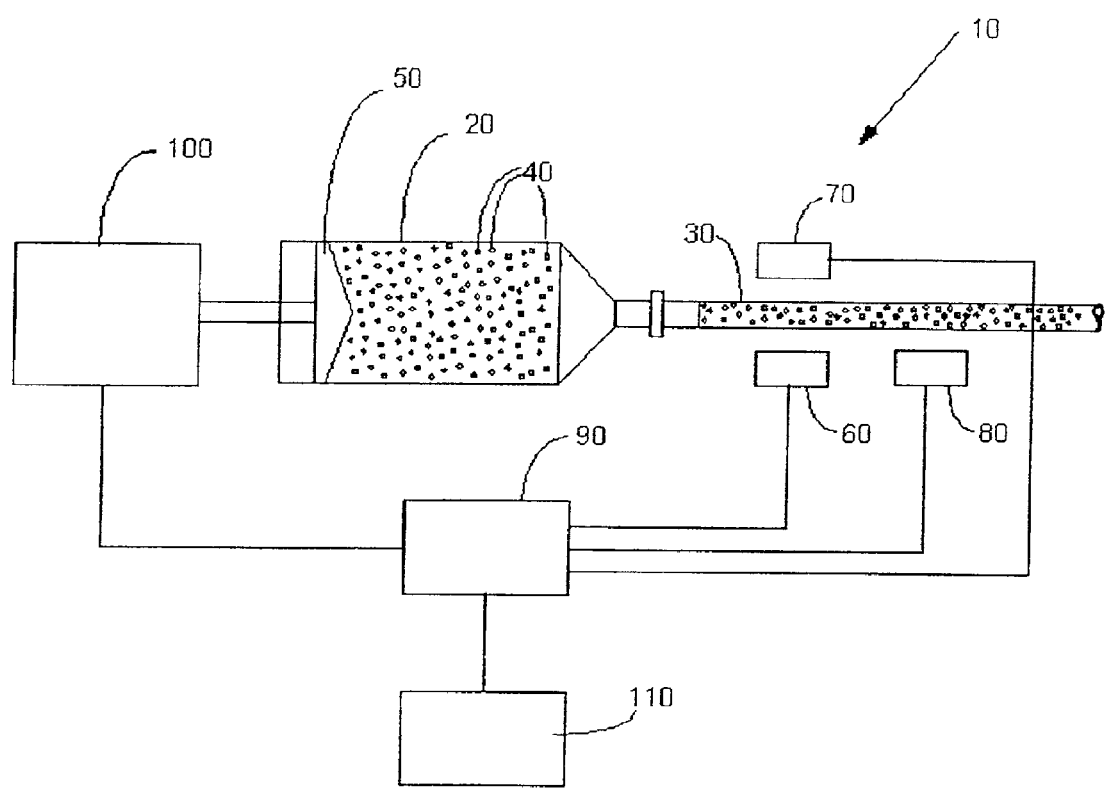
FIG. 1 illustrates an embodiment of a contrast enhancement agent concentration measurement system of the present invention.

FIG. 1 illustrates a system 10 including a syringe 20 and a connector tube 30 as part of the fluid path. As clear to one skilled in the art, however, it is possible to apply the systems and methods of the present invention to any type of fluid delivery system (for example, a peristaltic pump, a drip bag, a gear pump, etc.), whether automated or manually operated.

In FIG. 1, syringe 20 contains the contrast medium/enhancement agents including bubbles 40 and includes a moveable piston 50 for pressurizing the contrast medium. Connector tube 30 delivers the fluid from syringe 20 to the injection site on the patient, typically through an intravenous catheter. Connector tube 30 may be attached to syringe 20 with a connecting device such as a Luer fitting (not shown). Syringe 20 and connector tube 30 are preferably sterile to prevent bio-contamination or infection of the connected patient.

A sensor, for example, including an ultrasound emitter 60, is preferably attached to the wall of connector tube 30 to insonate the contents of connector tube 30 with ultrasound energy. Because it is preferable to make reliable contact to the wall of connector tube 30 to transmit the ultrasonic energy, a custom molded section of the fluid path may be used as will be discussed in detail later in relation to FIG. 3. It is also possible for elements of the sensor to be integrated with the connector tube or as part of a disposable element within the fluid path.

In this embodiment, the sensor also preferably includes an ultrasound receiver 70 positioned on the side of the connector tube 30 opposite emitter 60 to receive the transmitted ultrasound energy. Emitter 60 and receiver 70 can also be combined together as a single unit that, for example, clips onto connector tube 30. This arrangement is configured for operation in a transmissive mode. The functions of emitter 60 and receiver 70 can also be performed by a single unit which operates in a reflective mode. The reflective mode is basically how ultrasonic imaging units operate. A second emitter 80 can be used to insonate the fluid path to take advantage of beat frequency resonance effects of microbubbles 40 (described in further detail below). Or element 80 could operate as a receiver to receive some of the scattered energy.

A signal processor 90 (for example, including a microprocessor) can generate the transmitted ultrasound signal(s), amplify the received signal, determine the concentration of the agent 40 taking into consideration the arrangement that is used, and forward a control signal to, for example, an attached powered injector 100 and/or an operator display 110. The control signal can be used in various ways. One way is to increase the flow rate of the injection (ml/sec) if the concentration of the particles in the medium decreases so that a constant number of particles is delivered per second.

Several different types or modes of sensors or transmit/receive couplings are possible for use in the present invention depending on the elements that are included in the system. Several configurations or operating modes are described below for illustrative purposes.

Transmissive Operation

Transmissive operation is suitable for use with contrast enhancing agents that contain solid particles or exhibit ultrasound signal attenuation as a function of bubble concentration and/or size distribution. In this configuration, ultrasound energy is transmitted from an ultrasound emitter 60 and the transmitted energy is received directly across the fluid path with an ultrasound receiver 70. The presence of microbubbles 40 will scatter some of the transmitted energy so that only a portion of the transmitted energy is received depending on the microbubble concentration. (In FIG. 3, beams 119, 120, and 121 are scattered. Beam 122 is transmitted.) The decrease in transmissivity is also referred to as beam attenuation.

Figure 3:
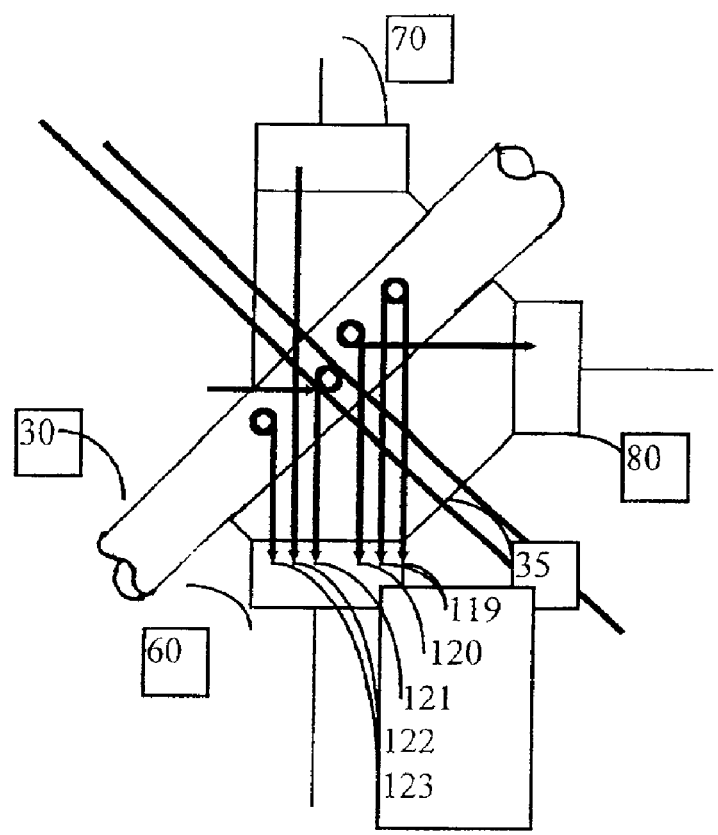
FIG. 3 illustrates an embodiment of a fluid path element adapted to optimally transmit energy to the fluid for measurement of microparticle concentration.

For enhancement agents that contain solid particles, in addition to scattering energy, the particles also absorb energy, which occurs by a mechanism referred to as "relative motion". (This is shown in FIG. 3, beam 123.) The change in attenuation caused by relative motion increases linearly with particle concentration and the square of the density difference between the particles and surrounding medium. Parker, K. J. et al., "A Particulate Contrast Agent with Potential for Ultrasound Imaging of Liver", *Ultrasound in Medicine and Biology*, Vol. 13, No. 9, p. 555, 561 (1987).

In one preferred embodiment, the transmitting and receiving elements can be physically attached together so that the tubing or other fluid path element can be secured between the two elements. Alternately, the two elements could be placed on a clip-on type assembly that clamps onto the tubing.

The ultrasound signal intensity of emitter 60 is preferably sufficient to measure changes in transmissivity or reflection/response, but not so great as to damage microbubbles 40 by excessive energy from the transducer of emitter 60. Otherwise the measurement itself can affect the microbubble concentration of the medium. However, if desired, emitter 60 can be operated with sufficient power to selectively destroy microbubbles 40 to control the concentration thereof.

Reflective Backscatter Operation

In this technique, the reflected backscatter from transmitted ultrasound energy is measured to determine microbubble concentration. Ultrasound energy is transmitted and the amount of backscatter that is received is measured. In FIG. 3, beam 119 is backscattered. Ultrasound energy may be transmitted and received by the same element, an ultrasound transmitter/receiver transducer. This mode is similar to, but much simpler than, the configuration used by ultrasound scanners. Only a single transmit/receive element is needed and there is no scanning of the element by either physical movement or phased array techniques. The amount of backscatter received from the transmitted energy is measured by signal processor 90 to determine the concentration of microbubbles 40 in the agent. When many bubbles 40 are present, the level of backscatter energy will be high. The amount of backscatter that is present is a function of a number of parameters including, for example, the liquid, bubble size, and frequency of ultrasound energy used, in addition to bubble concentration.

The capability of a substance to cause backscatter of ultrasound energy also depends on a number of other characteristics of the substance such as its ability to be compressed. Different substances are compared using a particular measure of the ability of a substance to cause backscatter known as "scattering cross section". The scattering cross section of a particular substance is proportional to the radius of the scatterer, and also depends on the wavelength (i.e., 1/frequency) of the ultrasound energy and on other physical properties of the substance. See U.S. Pat. No. 5,611,344. When many bubbles 40 are present, the level of backscatter energy will be high. Operation in a reflective backscatter mode has the added advantage that the Doppler shift from the moving bubbles can be measured if the vector of incidence of the ultrasonic energy has a sufficiently large component in the direction of the fluid flow. This then provides a measurement of flow rate. This information can be useful for flow rate control in non-syringe based pumps or for detecting conditions such as a fluid blockage or flow stall.

Reflective Harmonic Operation

A reflective harmonic operational configuration is similar to the configuration used for reflected backscatter operation, only the media is insonated by one frequency and backscatter is received at an harmonic or combination of harmonics of the transmitted frequency. (A harmonic of a frequency f is an integer multiple of f.) Depending on their size, at some frequencies, microbubbles 40 resonate with the applied ultrasound field. Bubbles 40 grow larger and/or become smaller in sympathy with the oscillations of pressure caused by the incident sound. For large enough power levels, the resonant oscillation in the ultrasound field contains non-linear motion of the bubble wall. This non-linear motion creates harmonic sounds that can be detected by an ultrasound transducer.

Harmonic mode imaging is used with some enhancement agents that show a distinct and relatively large response at harmonics of some excitation frequency. With this configuration, the transmitting element preferably has sufficient bandwidth to transmit and receive harmonics and sufficient sensitivity to detect the harmonic response. It may be preferable to have separate transmit and receive elements in this embodiment that are matched to the transmit and receive frequencies, respectively.

In addition, it is possible to gather information on bubble concentration as a function of bubble size in a liquid by sweeping the transmitting frequency and observing the harmonic response over a range of frequencies. The amplitude of the harmonic response is related to the concentration of bubbles of a certain size, since the resonant frequency of an individual bubble is a function of its size. This could be especially useful for use with harmonic imaging or drug delivery applications.

Configurations that are based on backscatter or harmonic measurement techniques may be more suitable for agents that contain a micro-particle substrate for the microbubbles (for example, Levovist™ available from Schering AG of Berlin, Germany). Because the substrate may still remain after bubbles are destroyed, backscatter techniques that look for response from the bubbles may give a better indication of bubble concentration than transmissive methods that can be affected by solid particles in the agent.

Reflective Beat Frequency Operation

Reflective beat frequency operation involves detecting the non-linear sum and difference beat frequencies produced by microspheres when two impinging signals with non-identical frequencies are combined by mixing. See U.S. Pat. No. 5,601,086. The technique applies to microsphere concentration in a body fluid or in a general fluid.

Referring to FIG. 3, transmitted energy from ultrasound emitter 60 is directed through connector tubing 30 to the fluid. A second emitter 80 is used to transmit energy at the same region at a second frequency that is also an approximate resonant frequency of the microspheres. The microspheres interact and emit the sum and difference of the two frequencies. Receiver 70 is used to detect the sum and difference frequencies that are a function of microbubble concentration.

Optical Diffusion Approach

Another operational approach is to detect changes in microbubble concentration by an optical diffusion measurement. In this application, electromagnetic radiation of many wavelengths (frequencies), even down to DC current, may be used. As with ultrasound, optical scatter is a function of the number of particles and their effective cross sectional scattering area. Again, FIG. 3 can be used for this discussion. A collimated light beam from an optical source or emitter 60, such as a laser diode or other light emitting device, can be coupled through a relatively transparent adapter 35 to a tube or container (segment of the fluid path) filled with the enhancement agent. The optical diffusion or scatter could be measured with an optical sensor/receiver oriented toward the container, such as a phototransistor element 70 or 80. The phototransistor may be connected to the input of an amplifier (not shown) to obtain a useable high level output signal.

For optimal scatter measurement, the optical sensor 80 can be oriented perpendicular to the beam from the optical source 60 so that the energy from the direct beam is not measured, and only the scattered component is measured. The chamber used is preferably as transparent as possible so as not to introduce any additional diffusion or reflective mirror effects from its interior surface. To eliminate potential noise effects of ambient light sources, the optical source and sensor are preferably shielded with an enclosure to absorb reflected light within. Alternatively, the optical source can be pulsed and the receiver can use a chopper amplifier, also known as a lock-in amplifier, to measure small changes in diffusion and reject measurement variations from ambient sources. Also, by using both detectors 70 and 80 it is possible to take the ratio of the scattered to the transmitted light and remain independent of variations in the intensity of the light source. This is important because light sources generally degrade over time and fluctuate with power supply variations.

Several other methods are possible for performing concentration measurements or particle size measurements for small agents in a suspension. These methods include laser reflection, diffraction, turbidity and photon migration approaches.

For particle substrate microbubble agents such as Levovist, it is believed that there will be some base component of scatter resulting from the particle substrate in the mixture and some additional scatter resulting from the microbubbles attached to the substrate. As the bubbles diffuse into the surrounding liquid or are destroyed, the optical diffusion properties of the media may change. It may be possible to obtain an adequate estimate of microbubble concentration by measuring only the concentration of the substrate particulate through scatter measurements. For agents that are relatively high in particle and microbubble density, it may be necessary to use a transparent container that has relatively small dimensions so that the scattered light is not reabsorbed by the surrounding volume of media. Another solution is to dilute the media by some known amount to reduce the degree of optical scatter that occurs or to increase the intensity of the optical source. It may also be possible to measure microbubble concentration changes by changes in transmissivity or optical density of the media. This approach will require an optical path length through the media that is long enough for changes in optical density to be detected, but short enough so that some signal gets through for the measurement.

Fluorescence of the microparticles is another mechanism that could be used to measure the concentration of the microparticles. Electromagnetic radiation of one wavelength is transmitted into the fluid, and emissions of another wavelength are emitted by the microparticles.

The methods disclosed above transmit energy into the fluid and measure transmission and/or reflection of that energy at some position. FIG. 3 illustrates these modes of measurement in general. In FIG. 3, element 60 is the source of the energy (ultrasound or electromagnetic energy). The energy can be received by elements 70 and/or 80 and/or 60. Element 35 couples the energy in a repeatable fashion into the fluid. In a preferred embodiment, element 35 is injection molded to have precise and repeatable dimensions. Normal extruded tubing is not typically repeatable enough, although precision extrusion techniques are possible. Alternatively, several paths (such as using both 60 to 70 and 60 to 80) can be used to compensate for extrusion variability. Element 35 can, for example, be molded into the neck of a syringe or can be part of the connector at either end of the tube used to conduct the fluid to the patient. It might also be possible to simply insert mold element 35 around the fluid path tubing 30. A preferable material for element 35 is polycarbonate, which is clear and easily injection moldable. For ultrasound transmission, polypropylene can also be used.

Figure 2:
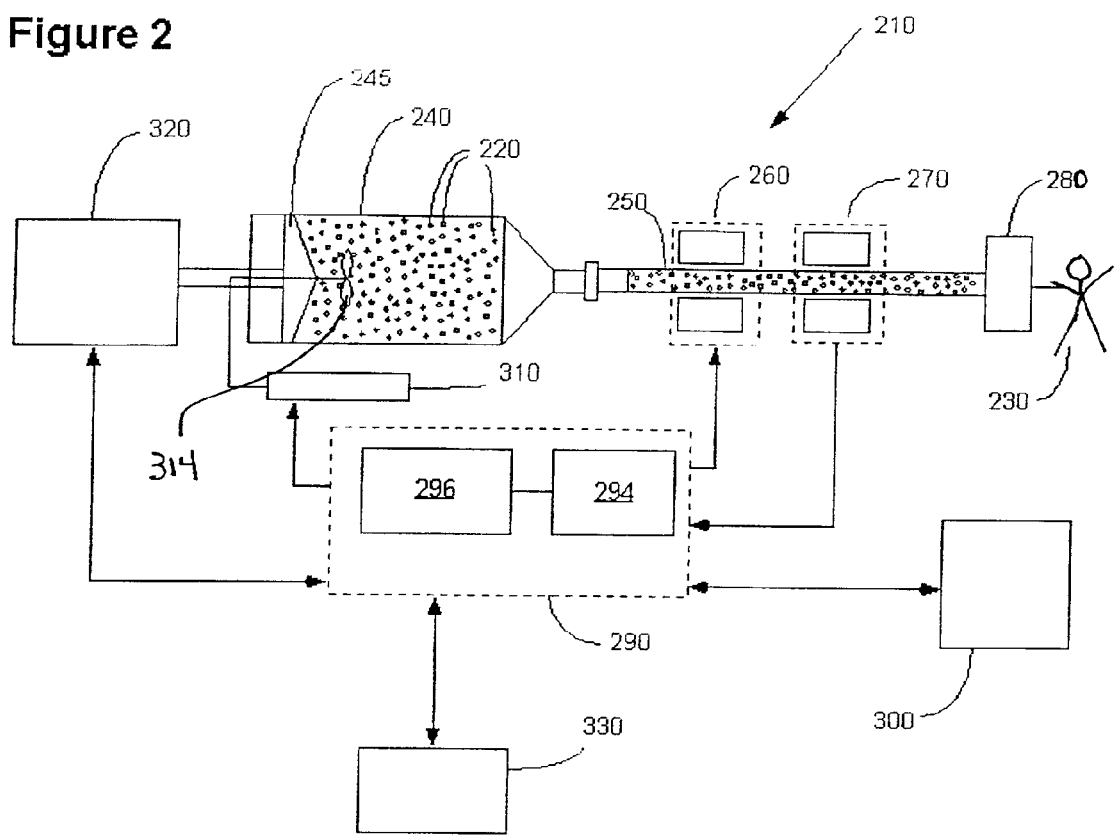
FIG. 2 illustrates an embodiment of a delivery system of the present invention.

Delivery System with Contrast Enhancement Agent Concentration Measurement and Operational Control FIG. 2 illustrates a block diagram of another embodiment of a delivery system 210 for delivering contrast enhancement agents (for example, a suspension of bubbles 220 in a fluid) to a patient 230. In this embodiment, a syringe or pressurizing vessel 240 drives fluid through a fluid path 250. Fluid path 250 may pass through a bubble or contrast enhancement agent concentration regulator 260 that can affect the enhancement properties of the agent by, for example, selectively destroying bubbles 220. Bubbles 220 may be destroyed, for example, by insonating the fluid with ultrasound energy, generating local temperature or pressure changes in the media or by mechanical agitation.

The ability to destroy microbubbles in the fluid path opens opportunities to improve and better control the imaging procedure. As discussed above, bubbles can be destroyed by insonating the agent with sufficient ultrasound energy, especially if the energy is at a resonant frequency of the bubbles of interest. Since mechanical resonance of a bubble wall is a function of bubble size, it may be possible with the proper power and frequency settings to selectively decrease the concentration of bubbles of a certain size. Such selective destruction allows control of the bubble size distribution. Microbubbles could be destroyed in the fluid path as part of a strategy to maintain a constant agent concentration.

Fluid path 250 continues through a concentration sensor 270 similar to that described in connection with FIG. 1, and then continues on through a patient interface 280 to an injection site on patient 230. The output of sensor 270 passes to a processing unit 290 which may, for example, include a concentration measurement and signal processing unit 294 to provide concentration data for use by delivery system 210 and an electronic control system 296. A signal corresponding to the concentration data may be sent from control system 296 to any number of devices in delivery system 210 including, for example, an imaging unit such as an ultrasound scanner 300. The control signal can be used, for example, to adjust the image (for example, by increasing or decreasing gain), to provide concentration information as part of documentation and/or to assist with diagnosis during the imaging procedure. Information can also preferably be sent from imaging unit 300 to control system 296 or processing unit 290 to, for example, control other devices such as, for example, an agitation mechanism 310 (including, for example, a mechanical stirrer 314) which homogenizes the concentration of particles in the fluid, a powered injection control unit 320 and/or concentration regulator 260. If the agitation mechanism were operated vigorously enough, the concentration of particles in the fluid could even be increased.

Agitation mechanisms suitable for use in the present invention are disclosed in a U.S. patent application entitled AGITATION DEVICES AND DISPENSING SYSTEMS INCORPORATING SUCH AGITATION DEVICES and filed on Mar. 12, 1999, the disclosure of which is incorporated herein by reference. In that regard, several commercial agents now available require some kind of agitation or mixing for preparation. These include, but are not limited to: Albunex™ and Optison™ available from Molecular Biosystems, Inc. of San Diego, Calif., and Levovist™.

The concentration measurement techniques of the present invention can be used during initial preparation of the medium or during an injection procedure to determine whether agitation/preparation is sufficient or as feedback for agitation or mixing control. Some agents, such as Levovist™, are known to precipitate or separate over time in some of the larger concentrations (for example, 400 mg/ml).

Concentration measurement techniques can be used, for example, to detect such separation and restart or increase agitation to help reduce precipitation effects.

Other agents, such as EchoGen™ available from SONUS Pharmaceuticals, Inc. of Bothell, Wash., require hypo-baric (pressure) activation before use. Typically, the agent is placed in a hand syringe, the fluid path is sealed and the plunger is pulled back and suddenly released, generating a pressure transient within the media. During this process, the perfluoro-compound in the agent converts to very small droplets (200 to 600 nm) and microbubbles. If this procedure is not performed adequately, image enhancement may be degraded and patient tolerance may decrease. Microbubble and/or droplet concentration can be measured after pressure activation for these units to ensure that the agent was prepared correctly and to give information on the remaining post-activation contrast enhancement agent life.

Concentration sensor 270 or multiple sensors can be located anywhere on the fluid delivery path from, for example, attachment to the barrel of syringe or pressurizing vessel 240 to patient interface 280. Attachment of a concentration sensor to the syringe or to a storage container wherein preparation of the contrast medium occurs can, for example, enable measurement of contrast enhancement agent concentration during preparation of the contrast medium, regardless of the mode or mechanism of initial preparation (for example, including hypobaric preparation or simple agitation). If concentration sensor 270 is located near the patient injection site at the end of fluid path 250, near the patient interface 280, one can account for microbubble degradation effects from shear rate, temperature and other delivery effects. Since sensor 270 preferably does not require direct contact with the contrast enhancement agent, a coupling piece can be made as a disposable part of a tubing set for convenience in attaching sensor 270 and to maintain sterility with patient interface 280. The sensing area is preferably a known volume or accessible area of the agent surface located on fluid path 250, as was discussed above in relation to FIG. 3.

As discussed above, control system 296 of processing unit 290 may use concentration data and other information to activate or control agitation mechanism 310, such as mechanical stirrer 314, so that the contrast enhancement agent is mixed homogeneously. Information from control system 296 can also be sent to injection controller 320 to dynamically adjust flow rate as a way to control the concentration of the contrast enhancement agent as it enters patient 230. The concentration and other data can also be sent to an optional user interface 330 so that the operator may receive information about the agent being delivered. Data, such as control parameters or algorithms, can also preferably be sent from user interface 330 to processing unit 290.

In summary, contrast enhancement agent concentration or other data can be used in a variety of applications. The systems described above, for example, may be used in a stand-alone embodiment with an operator interface or with a powered injection system to provide real-time feedback to the injector system for dynamic control of flow rate and delivery concentration. If the system is used in a stand-alone embodiment, it can be used with a simple operator interface to indicate when the contrast enhancement agent is properly prepared or is degraded. Contrast enhancement agents can degrade with time, for example, as a result of gas diffusion out of the bubble or a breakdown in the encapsulation mechanism. It has also been observed with some agents (for example, Levovist) that pressure from injection or blockage of the fluid path can potentially decrease the effectiveness of the agent, presumably by destroying some portion of the microbubbles. Agents can also lose their effectiveness through improper preparation techniques such as excessive agitation. Microbubble concentration is expected to decrease as the agent degrades. The present invention can be used to quickly indicate if there is a problem with the media, reducing the chance of an unnecessary procedure, or to indicate the remaining effective life of the contrast medium. Any number of visual, audio, or tactile means can be used to display or present the concentration measurement to the operator.

Real-time contrast enhancement agent concentration, size distribution or other data can assist in overcoming many current imaging limitations such non-linear blooming and shadowing effects, scanner-to-scanner gain variability and physiological time delays before enhancement. Bubble concentration data can also be used to control scanner settings, such as power, gain (for example, as a function of measured pixel density), time between successive scans and as other settings.

Time adjustments between scans may be especially useful because, for some agents, microbubbles are destroyed when insonated at sufficient ultrasound power settings needed to image the surrounding tissue. As an example, the time delay between scans can be automatically increased upon detection of low contrast enhancement agent concentration in the region-of-interest. This phenomenon may occur when additional time is required for a sufficient number of bubbles to congregate in the region-of-interest to give adequate enhancement. Such control will reduce the amount of signal loss resulting from bubble destruction. A scan interval controlled by contrast enhancement agent concentration can ensure sufficient and uniform enhancement from scan to scan, given the potential variability in injected concentration.

In the future, it is expected that microbubble agents may be used for more advanced diagnostic applications, such as site specific imaging and therapeutic applications, such as site specific or ultrasound activated drug delivery. The systems of the present invention will be very useful in these applications in which the contrast enhancement agent concentration can be measured as part of monitoring delivered drug dose.

Although the present invention has been described in detail in connection with the above embodiments and/or examples, it is to be understood that such detail is solely for that purpose and that variations can be made by those skilled in the art without departing from the spirit of the invention. The scope of the invention is indicated by the following claims, rather than by the foregoing description. All changes or modifications which come within the meaning and range of equivalency of the claims are to be embraced within their scope.

What is claimed is:

1. A method of preparing a medium with contrast enhancement agents therein, the method comprising the step of measuring a property of the contrast enhancement agents during preparation of the medium; and controlling at least one parameter of the preparation during preparation of the medium at least in part based upon the measured property.

2. The method of claim 1, further comprising the step of pressurizing the medium.

3. The method of claim 1, further comprising the step of producing an image of a patient.

4. The method of claim 1, further comprising the step of agitating the medium.

5. The method of claim 1 wherein the property of the contrast enhancement agents comprises at least one of concentration and size distribution.

6. A system for preparing a medium with contrast enhancement agents therein, the system comprising:
   a container including the medium;
   an agitation mechanism operably associated with the container for agitating the medium; and
   a sensor adapted to measure a property of the contrast enhancement agents in the container; and a controller operable to control a parameter of the preparation of the medium during preparation of the medium at least in part in on the basis of the measured property.

7. The system of claim 6, further comprising a communication unit in communication with the sensor, the communication unit operable to communicate data corresponding to the measured property of the contrast enhancement agents.

8. The system of claim 7, further comprising a processing unit in communication with the communication unit, the processing unit operable to transmit one or more control signals based at least in part on the measured property data.

9. The system of claim 8, wherein the controller is in communication with the processing unit, the controller operable to control the agitation mechanism at least in part in response to the one or more control signals from the processing unit.

10. The system of claim 6 wherein the property of the contrast enhancement agents comprises at least one of concentration and size distribution.

11. The system of claim 7, further comprising a user interface in communication with the communication unit to provide an indication functionally related to the measured property data to an operator.

12. A method of delivering a medium with contrast enhancement agents therein into a patient, the method comprising:
   measuring a property of the contrast enhancement agents; and
   using the measure property to control at least one of the delivery of the contrast enhancement agents or an imaging procedure carried out in conjunction with delivery of the contrast enhancement agents by selective destruction of contrast enhancement agents.

13. The method of claim 12 wherein the selective destruction adjusts the concentration of the contrast enhancement agents.

14. The method of claim 12 wherein the selective destruction adjusts the size distribution of the contrast enhancement agents.

15. A method of delivering a medium with contrast enhancement agents therein to a patient during an injection procedure, the method comprising:
   measuring a property of the contrast enhancement agents during delivery to the patient during the injection procedure; and
   selectively destroying one or more of the contrast enhancement agents to control the measured property.

16. The method of claim 15 wherein the measured property is concentration.

17. The method of claim 16 wherein the one or more contrast enhancement agents are destroyed to control concentration.

18. The method of claim 15 wherein the measured property is size distribution.

19. The method of claim 18 wherein the one or more contrast enhancement agents arc destroyed to control size distribution of the agents.

20. A fluid delivery system comprising:
   a pressurizing device for pressurizing a fluid medium comprising a suspension of two materials;
   a fluid path connecting the pressurizing device to a patient;
   a sensor operably associated with at least one of the pressurizing device or the fluid path, the sensor operable to measure a property of the fluid medium;
   a communication unit in communication with the sensor, the communication unit operable to communicate data corresponding to the measured property of the fluid medium;
   a processing unit in communication with the communication unit, the processing unit operable to transmit one or more control signals based at least in part on the measured property data; and
   a controller in communication with the processing unit, the controller operable to control the pressurizing device at least in part in response to the one or more control signals from the processing unit.

21. The system of claim 20 wherein at least one of the two materials comprises contrast enhancement agents.

* * * * *